US008801993B2

(12) United States Patent
Padsalgikar et al.

(10) Patent No.: US 8,801,993 B2
(45) Date of Patent: Aug. 12, 2014

(54) POLYURETHANE HEADER FORMED DIRECTLY ON IMPLANTABLE ELECTRICAL DEVICES

(75) Inventors: Ajay D. Padsalgikar, Plymouth, MN (US); Elenora Stepanova, Notting Hill (AU); Richard Anup D'Mello, Clayton South (AU); Jadwiga Weksler, Blackburn (AU)

(73) Assignee: Aortech International plc, Weybridge Surrey (GB)

( * ) Notice: Subject to any disclaimer, the term of this patent is extended or adjusted under 35 U.S.C. 154(b) by 0 days.

(21) Appl. No.: 13/504,589

(22) PCT Filed: Oct. 22, 2010

(86) PCT No.: PCT/AU2010/001406
§ 371 (c)(1),
(2), (4) Date: Jul. 16, 2012

(87) PCT Pub. No.: WO2011/050396
PCT Pub. Date: May 5, 2011

(65) Prior Publication Data
US 2012/0271388 A1    Oct. 25, 2012

Related U.S. Application Data

(60) Provisional application No. 61/256,115, filed on Oct. 29, 2009.

(51) Int. Cl.
*B29C 45/14*    (2006.01)
(52) U.S. Cl.
USPC .................................. 264/272.14; 264/328.6
(58) Field of Classification Search
USPC ............... 264/328.6, 272.11, 272.14, 272.21; 607/36
See application file for complete search history.

(56) References Cited

U.S. PATENT DOCUMENTS

| 4,647,643 A | 3/1987 | Zdrahala et al. |
| 5,679,026 A | 10/1997 | Fain et al. |

(Continued)

FOREIGN PATENT DOCUMENTS

| JP | 4504513 A | 8/1992 |
| JP | 5184688 A | 7/1993 |

(Continued)

OTHER PUBLICATIONS

International Application Serial No. PCT/AU2010/001406, International Preliminary Report on Patentability mailed Mar. 5, 2012, 14 pgs.

(Continued)

*Primary Examiner* — Jill Heitbrink
(74) *Attorney, Agent, or Firm* — Schwegman, Lundberg & Woessner, P.A.

(57) ABSTRACT

This invention relates to electrical devices that are implantable inside an animal, including humans. The invention particularly relates to polyurethane headers mounted on the electrical devices to house electrical contacts. The polyurethane headers are formed by (a) mixing (i) a prepolymer comprising a silicon-containing diol of formula (I) in which $R_1$, $R_2$, $R_3$ and $R_4$ are independently selected from $C_{1-6}$alkyl; $R_5$ and $R_6$ are independently selected from $C_{1-6}$alkylene; $R_7$ is $C_{1-6}$alkylene, O, S or NR in which R is H or $C_{1-6}$alkyl; and n is 1 to 3 and a diisocyanate; and (ii) a $C_{2-12}$alkanediol; (b) injecting the mixture of the prepolymer and the $C_{2-12}$alkanediol into a mold having a cavity shaped to form a header; (c) allowing the mixture to cure and form a polyurethane header within the mold; and (d) releasing the formed polyurethane header from the mold.

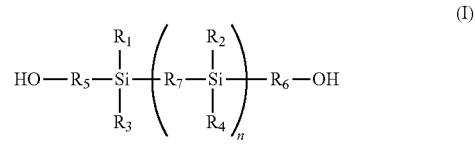

18 Claims, 2 Drawing Sheets

(56) References Cited

U.S. PATENT DOCUMENTS

| | | |
|---|---|---|
| 2004/0122481 A1 | 6/2004 | Tidemand et al. |
| 2007/0027285 A1 | 2/2007 | Gunatillake et al. |
| 2009/0012576 A1 | 1/2009 | Erbstoeszer et al. |
| 2009/0118778 A1 | 5/2009 | Biggs, Jr. et al. |

FOREIGN PATENT DOCUMENTS

| | | |
|---|---|---|
| JP | 10137346 A | 5/1998 |
| JP | 2001500912 A | 1/2001 |
| JP | 2001510196 A | 7/2001 |
| JP | 2002508682 A | 3/2002 |
| JP | 2002509958 A | 4/2002 |
| JP | 2006501959 A | 1/2006 |
| JP | 2007512398 A | 5/2007 |
| JP | 2008505729 A | 2/2008 |
| JP | 2009531474 A | 9/2009 |
| JP | 2009532102 A | 9/2009 |
| JP | 2010516404 A | 5/2010 |
| WO | WO-9903863 A1 | 1/1999 |
| WO | WO-9950327 A1 | 10/1999 |
| WO | WO-2004033516 A1 | 4/2004 |
| WO | WO-2005052019 A1 | 6/2005 |
| WO | WO-2007112485 A1 | 10/2007 |
| WO | WO-2011050396 A1 | 5/2011 |

OTHER PUBLICATIONS

International Application Serial No. PCT/AU2010/001406, International Search Report mailed Dec. 20, 2010, 4 pgs.

International Application Serial No. PCT/AU2010/001406, Response filed Apr. 21, 2011 to International Search Report and Written Opinion mailed Dec. 20, 2010, 4 pgs.

International Application Serial No. PCT/AU2010/001406, Written Opinion mailed Dec. 20, 2010, 8 pgs.

European Application Serial No. 10825842.7, Examination Notification Art. 94(3) mailed Jan. 16, 2014, 3 pgs.

European Application Serial No. 10825842.7, Extended European Search Report mailed Aug. 20, 2013, 4 pgs.

Japanese Application Serial No. 2012-535544, Office Action mailed Aug. 13, 2013, 10 pgs.

POLYURETHANE HEADER FORMED DIRECTLY ON IMPLANTABLE ELECTRICAL DEVICES

RELATED APPLICATIONS

This application is a nationalization under 35 U.S.C. 371 of PCT/AU2010/001406, filed Oct. 22, 2010 and published as WO 2011/050396 A1 on May 5, 2011. which claims priority to U.S. Provisional Patent Application Ser. No. 61/256,115, filed Oct. 29, 2009; which applications and publication are incorporated herein by reference in their entirety.

FIELD

This invention relates to electrical devices that are implantable inside an animal, including humans. Such devices include, but are not limited to, cardiac pacing devices or neurological stimulation devices. The invention particularly relates to plastics headers mounted on the electrical devices to house electrical contacts.

BACKGROUND

Implantable cardiac pacing devices or neurological stimulation devices comprise a metallic can holding the electronics. Electrical leads carry signals generated by the electronics to designated tissue or nerve sites so the signals stimulate the tissue or the nerve.

The electrical leads are connected to the metallic can during a surgical implant procedure. A connector assembly is formed on the metallic can for connecting the electronics to the leads. This assembly is encapsulated by an insulating and relatively fluid impermeable plastics material. The connector assembly is referred to as a header.

A range of different materials and their associated processing techniques are used to form headers. For example, epoxy materials are used as headers in certain applications. Epoxies have very long reaction time and can take hours to cure before they can be released from a mould.

As another example, hard grade polyurethane headers are used widely but they are exclusively used in the process of injection moulding. The process of injection moulding uses a high viscosity melt of a pre-formed polymer and this prevents good bonding to the electronic components and insulators. Therefore, the injection moulding happens as a separate step and the header is then mechanically or adhesively fixed on to the can.

For epoxies and polyurethanes, the manufacturing process of the header component is laborious, time consuming and ultimately unsatisfactory.

There is a need to provide an improved method of forming headers for implantable devices.

SUMMARY

In one aspect there is provided a method of forming a polyurethane header on a device that is implantable in an animal, the method comprising the steps of:

(a) mixing
  (i) a prepolymer comprising a silicon-containing diol of formula (I)

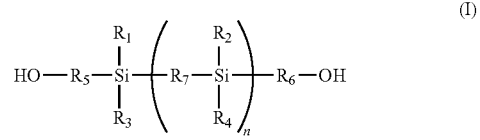

(I)

in which
  $R_1$, $R_2$, $R_3$ and $R_4$ are independently selected from $C_{1-6}$alkyl;
  $R_5$ and $R_6$ are independently selected from $C_{1-6}$alkylene;
  $R_7$ is $C_{1-6}$alkylene, O, S or NR in which R is H or $C_{1-6}$alkyl; and
  n is 1 to 3
  and
  a diisocyanate; and
  (ii) a $C_{2-12}$alkanediol
(b) injecting the mixture of the prepolymer and the $C_{2-12}$alkanediol into a mould having a cavity shaped to form a header;
(c) allowing the mixture to cure and form a polyurethane header within the mould; and
(d) releasing the formed polyurethane header from the mould.

The applicant recognises, generally speaking, that significant handling problems are created by pre-forming polyurethane and then remelting it for injection moulding of headers. Specifically, injection moulding is only viable when the pre-formed polyurethane is in a molten state at a temperature around 200° C. and, even then, the molten polyurethane is so viscous that considerable pressures are required to drive the molten polyurethane into moulds to form headers.

The applicant also recognises that polyurethanes formed of the silicon-containing diol of formula (I) defined above, a diisocyanate and $C_{2-12}$ alkanediol are non-elastomeric and have high flexural modulus, tensile strength and Shore hardness and have biocompatibility and biostability that are particularly advantageous for use as a header on implantable devices. The term "non-elastomeric" refers to polyurethanes having a % elongation up to 200%, preferably up to 100%. In addition, such a polyurethane can be produced as a transparent plastics header to assist with connection of electrical leads to electrical connectors of the device.

The applicant realises that transparency can be retained and formability can be improved by re-ordering preparation steps by forming a prepolymer by mixing a silicon-containing diol of formula (I) with a diisocyanate before mixing the prepolymer with a $C_{2-12}$ alkanediol. The mixture of the prepolymer and the alkanediol can then be injected into a mould at lower temperatures and under lower pressures than compared with the temperatures and pressures required to injection mould pre-formed polyurethane formed from the same components. Nevertheless, the reordered preparation steps produce a similar polymer with similar physical properties.

The device may form part of the mould to be at least partly exposed to the cavity, wherein step (c) causes the header to form on the device.

Injection of the mixture of the prepolymer and the alkanediol into the mould in contact with the device improves bonding with the device because the low viscosity of the mixture allows it to work into microscopic surface relief of the device. Upon curing, the header becomes mechanically interlocked with the surface relief and has a high bond strength with metals (eg. 16.7 MPa, 2422 psi: lap shear strength on titanium), polymers or ceramics. Additionally, the isocyanate groups in the mixture will chemically react with oxides on the surface of the device. This reaction further improves bonding of the header to the device.

The method may involve, in step (a), mixing the alkanediol with the prepolymer up to a limit after which the resultant polyurethane is translucent or opaque.

The weight ratio of silicon-containing diol: alkanediol may be at least about 75:25. However, the weight ratio may be in the range of 80:20 to 98:2 or 80:20 to 90:10. Specific weight ratios include 80:20, 88:45:11.55 and 90:10.

Suitable diols for the polyurethane contain 1,3-bis(4-hydroxybutyl)tetramethyldisiloxane (BHTD) as the silicon-containing diol and 1,4-butanediol (BDO) and cyclohexyl dimethanol CHDM as the $C_{4-12}$ alkanediol.

The diisocyanate is preferably 4,4'-diphenylmethane diisocyanate (MDI).

The ratio of prepolymer to alkanediol may be in the range of 5:1 to 20:1.

The mixing step (a) may be performed in any suitable mixing apparatus such as a mixing chamber.

The method may further comprise chilling the mould.

The prepolymer may have a viscosity in the range of 3,000 to 4,000 centipoise at around 70° C. and may be injected into a mixing apparatus under a pressure of 10 to 12 bar.

The alkanediol may have a viscosity in the range of 80 to 120 centipoise at room temperature and may be injected into a mixing apparatus under a pressure of 1 to 3 bar.

The prepolymer and the alkanediol may be injected into a mixing apparatus at respective temperatures such that they produce a mixture having a temperature that is below a temperature that adversely affects operation of the device.

Electronics contained within implantable devices can be destroyed when exposed to high temperatures such as above 60° C. typical of processes that involve injection moulding pre-formed polyurethane. The applicant has found that separate injection of the polyurethane forming components enables the header to be formed and cured at relatively low temperatures that are suitable for forming the header on the device. This avoids the need to form the header separately and then secure the header to the device as a separate processing step.

The prepolymer may be injected into a mixing apparatus at a temperature in the range of 70-90° C.

The alkanediol may be injected into a mixing apparatus at a temperature in the range of 25-40° C.

The applicant has further found that cure time is significantly reduced from around 6 hours.

Steps (c) and (d) may involve allowing the header to cure in the mould for no more than 20 minutes.

The cure time may be less than 15 minutes and, optionally, may be less than 10 minutes.

Without wishing to be held to any particular theory, the applicant believes that the cure time is reduced in part by vigorous mixing of the components before injection into the mould. While there may be other reasons for the shortened cure time, it is clear that productivity can be improved because headers can be released from moulds sooner, thereby enabling moulds to be reused in shorter turn-around times.

In another aspect there is provided a device that is implantable in an animal to electrically stimulate tissue, the device comprising:

(a) a can housing electronics capable of producing electrical signals;
(b) electrical connectors external of the can and in electrical connection with the electronics; and
(c) a polyurethane header in which the electrical connectors are embedded, the polyurethane header being formed by the method described above.

The device may further comprise electrical leads for linking the electrical connectors to the tissue and wherein the header has one or more recesses for receiving and linking the electrical leads to the electrical connectors.

BRIEF DESCRIPTION OF THE DRAWINGS

An embodiment of the invention will now be described, by way of example only, with reference to the accompanying drawings, in which.

DETAILED DESCRIPTION OF AN EMBODIMENT

Figure 1:
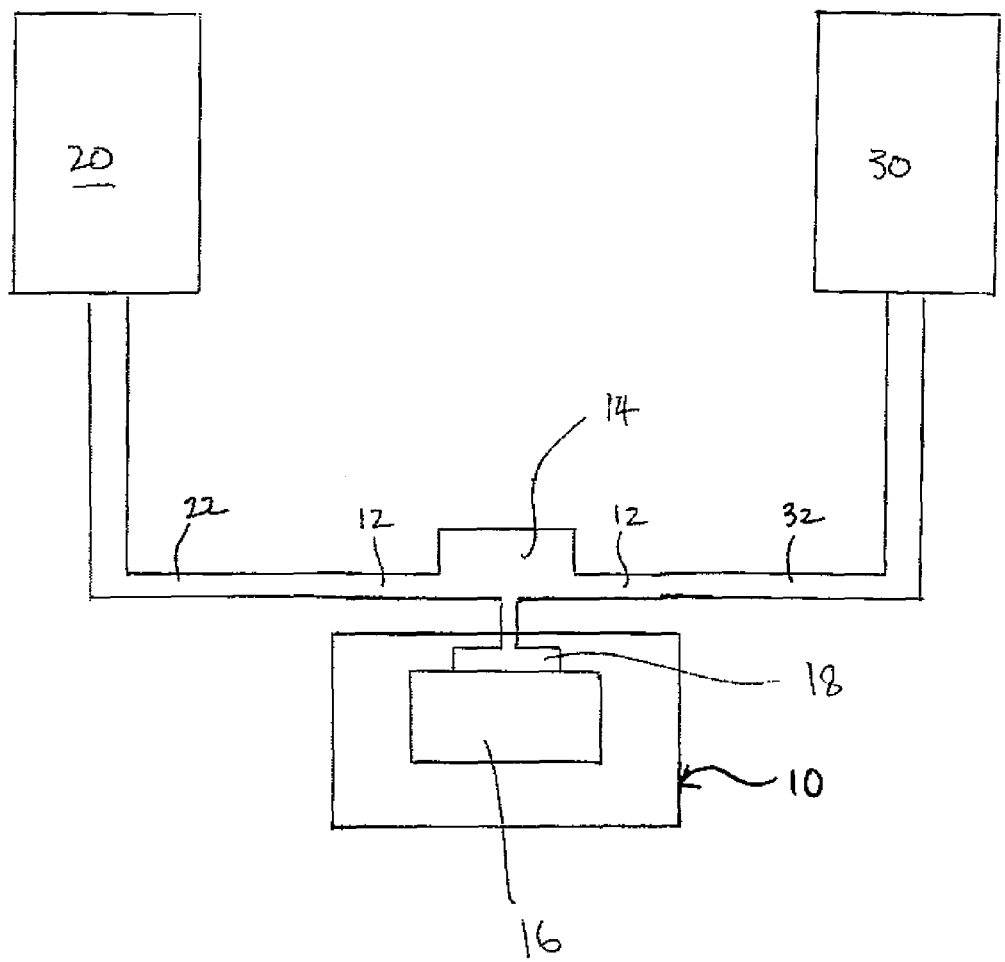
FIG. 1 is a schematic diagram of an apparatus for carrying out the method according to the invention.

Headers for implantable devices are formed in accordance with an embodiment of the invention by mixing a prepolymer and an alkanediol and then injecting the mixture into a suitable mould 10 according to FIG. 1.

The mould 10 receives a mixture of prepolymer and alkanediol from a mixing chamber 14. The mixing chamber 14 receives metered amounts of prepolymer from source 20 via conduit 22 and inlet 12 and of alkanediol from source 30 via conduit 32 and associated inlet 12. The prepolymer comprises a combination of the silicon-containing diol of formula (I) comprising BHTD and MDI and a $C_{4-12}$ alkanediol comprising BDO or CHDM in a molar ratio suitable for producing a transparent polyurethane header. The ratio may be around 80:20, but higher and slightly lower ratios are also suitable.

The prepolymer and alkanediol are mixed together in the mixing chamber 14 and are then forced into a linked mould chamber 16 by a continued supply of prepolymer and diisocyanate to the mixing chamber 14.

The mould chamber 16 is formed to accommodate an implantable device and is formed to leave a vacant cavity 18 when the implantable device is placed in the mould chamber 16 so that electrical connectors on the implantable device, in the form of electrodes, project into the cavity 18. Accordingly, prepolymer and alkanediol mixture flowing into the cavity 18 embeds the electrodes and contacts the surface of the implantable device that is exposed to the cavity 18.

Mixing of the prepolymer and alkanediol continues as they flow from the mixing chamber 14 and into the cavity 18. This flow causes intimate mixing, thereby reducing overall reaction time and cure time. Depending on the composition of prepolymer and the alkanediol, the cure time is generally less than 20 minutes and is typically less than 10 minutes. Once cured, the implantable device is released from the mould 10 by opening the mould 10 and removing the implantable device with the formed header.

Figure 2:
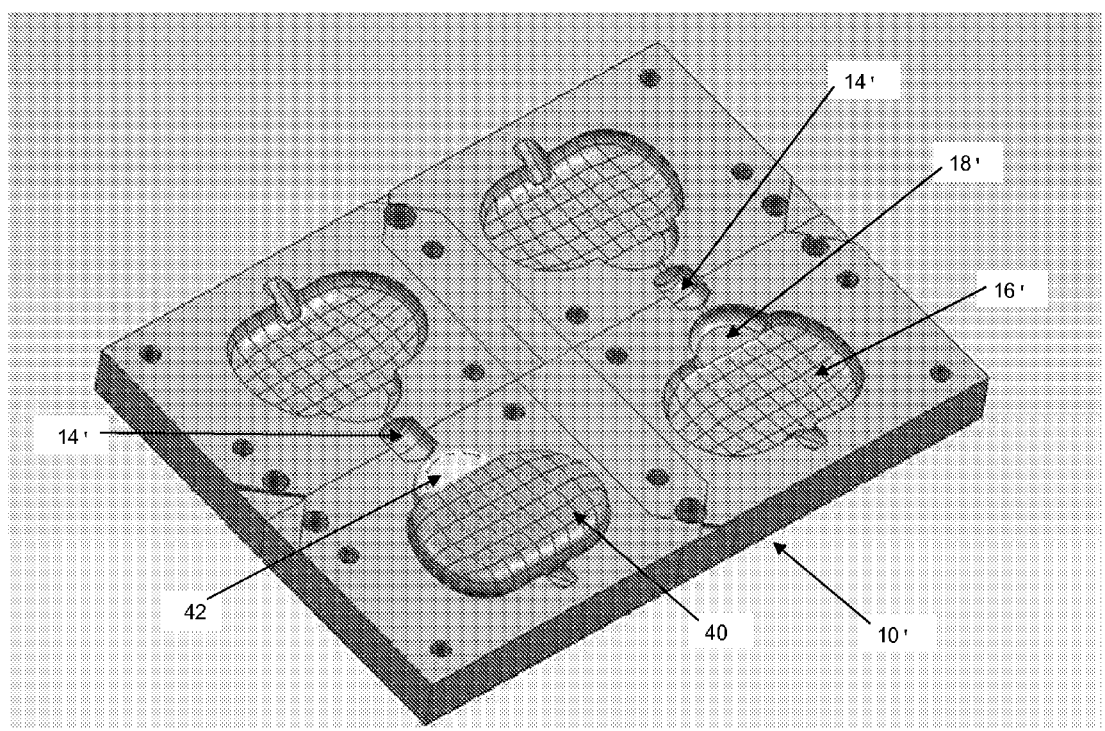
FIG. 2 is an isometric view of one side of four moulds according to an embodiment of the invention, with an implantable device located in one mould.

While the mould 10 in FIG. 1 shows a single header mould, moulds may be configured to produce batches of headers on implantable devices. An example of one side of a batch mould 10' is shown in FIG. 2 in which like features to the mould 10 in FIG. 1 are denoted with like numerals having a prime (')

suffix. In addition, FIG. 2 shows a header 42 formed on an implantable device 40 in the mould 10'.

Prior to injection into the mould 10, the mixture of the prepolymer and the alkanediol have respective viscosities and temperatures suitable for injection into a mould. While it will be appreciated that the viscosities and temperatures will vary depending on the composition of each, a prepolymer comprising BHTD and MDI can be controlled to have a viscosity of around 3-4,000 centipoise at a temperature in the range of 70° C. to 90° C. This viscosity is suitable for handling in injection moulding processes by injection under pressure of 10-12 bar.

The alkanendiol comprising BDO can be controlled to have a viscosity of around 100 centipoise at a temperature in the range of 25° C. to 40° C. and can be injected into the mixing chamber 14 under pressures of 1 to 3 bar.

Curing of the prepolymer with the alkanediol within the mould results in polyurethane being produced in situ in the mould. This avoids problems associated with preparing the polyurethane and then heating it to a temperature at which it is suitable for injection moulding. Such temperatures are greater than the temperatures at which electronics in implantable devices are rendered inoperable.

The process of injecting the mixture of the prepolymer and alkanediol into the mould enables the temperature inside the mould to be maintained in a range that does not affect electronics in implantable devices. While moulds may be chilled to account for the exothermic nature of the reaction between the prepolymer and alkanediol, the reduced temperature of the mould does not interfere with the capacity to inject the prepolymer and the alkanediol into the mould. As a result, headers can be moulded directly onto implantable devices, thereby avoiding the need for a subsequent processing step to secure pre-formed headers to implantable devices. The direct moulding also contributes to an observed improvement in bonding of headers to implantable devices.

It will be appreciated that, while FIGS. 1 and 2 illustrate moulds in accordance with an embodiment of the invention, any suitable mould may be used provided that the prepolymer and the alkanediol are mixed and then injected into the mould and they cure in the mould.

The prepolymer is a reaction product of the silicon-containing diol of formula (I) and a diisocyanate.

The amount of prepolymer present is preferably 85-92 wt %, more preferably 88-90 wt % based on the total weight of the polyurethane.

The term "$C_{1-6}$ alkyl" as used in formula (I) refers to straight chain, branched chain or cyclic hydrocarbon groups having from 1 to 6 carbon atoms, preferably 1 to 4 carbon atoms, more preferably methyl. Examples include alkyl groups such as methyl, ethyl, propyl, isopropyl, butyl, isobutyl, sec-butyl, tert-butyl, pentyl, neopentyl and hexyl or cycloalkyl groups such as cyclopropyl, cyclobutyl, cyclopentyl and cyclohexyl.

The term "$C_{1-6}$ alkylene" as used in formula (I) refers to divalent straight chain, branched chain or cyclic hydrocarbon groups having from 1 to 6 carbon atoms, more preferably 1 to 4 carbon atoms. Examples include ethylene, propylene, butylene, pentylene, hexylene, heptalene, octylene, cyclopropylene, cyclopentylene and cyclohexylene.

Suitable silicon-containing diols of formula (I) include those in which $R_1$ to $R_4$ are methyl, $R_5$ and $R_6$ are the same and selected from propylene and butylene, $R_7$ is selected from O or ethylene and n is 1. Preferred silicon-containing diols of formula (I) are BHTD (compound of formula (I) in which $R_1$, $R_2$, $R_3$ and $R_4$ are methyl, $R_5$ and $R_6$ are butylene, $R_7$ is O and n is 1), 1,4-bis(3-hydroxypropyl)tetramethyl disilylethylene (compound of formula (I) in which $R_1$, $R_2$, $R_3$ and $R_4$ are methyl, $R_5$ and $R_6$ are propylene, $R_7$ is ethylene and n is 1) and 1,4-bis(3-hydroxypropyl)tetramethyl disiloxane (compound of formula (I) in which $R_1$, $R_2$, $R_3$ and $R_4$ are methyl, $R_5$ and $R_6$ are propylene, $R_7$ is O and n is 1) more preferably BHTD.

The diisocyanate may be an aliphatic, cyclic or aromatic diisocyanates such as, for example, MDI, methylene biscyclohexyl diisocyanate ($H_{12}$MDI), p-phenylene diisocyanate (p-PDI), trans-cyclohexane-1,4-diisocyanate (CHDI), 1,6-diisocyanatohexane (DICH), 1,5-diisocyanaton-aphthalene (NDI), para-tetramethylxylenediisocyanate (p-TMXDI), meta-tetramethylxylene diisocyanate (m-TMXDI), 2,4-toluene diisocyanate (2,4-TDI) isomers or mixtures thereof or isophorone diisocyanate (IPDI). Aromatic diisocyanates such as MDI are preferred due their propensity to form uniform hard blocks that contribute both to good mechanical properties as well as biostability.

The $C_{4-12}$alkanediol may be BDO, 1,6-hexanediol, 1,8-octanediol, 1,9-nonanediol, 1,10-decanediol or 1,12-dodecanediol, preferably a $C_{4-10}$alkane diol, more preferably BDO.

The amount of alkanediol present is preferably 8-15 wt %, more preferably 10-12wt % based on the total weight of the polyurethane.

In a preferred embodiment, the polyurethane header is the reaction product of a prepolymer comprising BHTD and MDI and BDO. An example of such a polyurethane is Elast-Eon4™ marketed by the applicant. Polyurethanes of this type contain properties set out in Table 1 below which make them suitable for use in forming the headers of the present invention.

TABLE 1

| Property | Value |
| --- | --- |
| Hardness | 75-80 D |
| Ultimate Tensile Strength | 55-62 MPa |
| Ultimate Elongation | 18-25% |
| Flexural modulus | 1750-1950 MPa |

EXAMPLES

The invention will now be described with reference to the following non-limiting examples.

Example 1

Polyol Ratio, 80:20, BHTD:BDO

Method for preparing 500 grams of material:
The prepolymer is made by mixing MDI with BHTD, using a mechanical stirrer at 500 rpm for 2.5 minutes. The prepolymer is poured into source 20 of the mould 10 and degassed for 30-60 minutes at 70° C. to remove any bubbles. Once the prepolymer is degassed, source 20 is pressurised with nitrogen gas to a pressure of 2 bar and the temperature is increased to 80° C. Source 30 is filled with BDO.

Initially the pump throughput of the mould is set to 70 rpm, once the mould has stabilised the mixing chamber 14 is enabled and the throughput is reduced to 30 rpm. The mixture is then injected into the mould.

The pump is calibrated by adjusting the gears on the pump. The ratio of prepolymer to BDO is checked. For this example the ratio is set to 10.41:1, Prepolymer:BDO.

Example 2

Polyol Ratio, 90:10, BHTD:BDO

Method for preparing 500 grams of material:

The prepolymer is made by mixing MDI with BHTD, using a mechanical stirrer at 500 rpm for 2.5 minutes. The prepolymer is poured into source 20 of the mould 10 and degassed for 30-60 minutes at 70° C. to remove any bubbles. Once the prepolymer is degassed, source 20 is pressurised with nitrogen gas to a pressure of 2 bar and the temperature is increased to 80° C. Source 30 is filled with BDO.

Initially the pump throughput of the mould is set to 70 rpm, once the mould has stabilised the mixing chamber is enabled and the throughput is reduced to 30rpm. The mixture is then injected into the mould.

The pump is calibrated by adjusting the gears on the pump. The ratio of prepolymer to BDO is checked. For this example the ratio is set to 19.94:1, Prepolymer:BDO.

Example 3

Polyol Ratio, 88.45:11.55, BHTD:CHDM.

Method for preparing 60-100 grams of material:

The prepolymer is made by mixing MDI with BHTD, using a magnetic stirrer, under vacuum for 1.5 minutes. CHDM is added to the prepolymer and it is mixed under vacuum for a further 30 seconds. The mixture is then injected, manually, into a mould having a cavity shaped to form a header.

In the claims which follow and in the preceding description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

The invention claimed is:

1. A method of forming a polyurethane header on a device that is implantable in an animal, the method comprising the steps of:
    (a) mixing
        (i) a prepolymer comprising a mixture of a silicon-containing diol of formula (I)

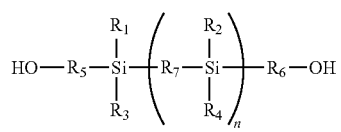

in which
$R_1$, $R_2$, $R_3$ and $R_4$ are independently selected from $C_{1-6}$alkyl;
$R_5$ and $R_6$ are independently selected from $C_{1-6}$alkylene;
$R_7$ is $C_{1-6}$alkylene, O, S or NR in which R is H or $C_{1-6}$alkyl; and
n is 1 to 3 and
a diisocyanate; and
        (ii) a $C_{2-12}$alkanediol
    (b) injecting the mixture of the prepolymer and the $C_{2-12}$alkanediol into a vacant cavity of a mould chamber comprising an implantable device that comprises electrodes that project into the vacant cavity, wherein the vacant cavity is shaped to form a header;
    (c) allowing the mixture to cure and form a polyurethane header within the vacant cavity so that the header is secured to the implantable device and embeds the electrodes; and
    (d) releasing the implantable device and the formed polyurethane header from the mould.

2. The method according to claim 1, in which the silicon-containing diol of formula (I) is selected from those in which $R_1$ to $R_4$ are methyl, $R_5$ and $R_6$ are the same and selected from propylene and butylene, $R_7$ is selected from O or ethylene and n is 1.

3. The method according to claim 2, in which the silicon-containing diol of formula (I) is BHTD (compound of formula (I) in which $R_1$, $R_2$, $R_3$ and $R_4$ are methyl, $R_5$ and $R_6$ are butylene, $R_7$ is O and n is 1), 1,4-bis(3-hydroxypropyl)tetramethyl disilylethylene (compound of formula (I) in which $R_1$, $R_2$, $R_3$ and $R_4$ are methyl, $R_5$ and $R_6$ are propylene, $R_7$ is ethylene and n is 1) or 1,4-bis(3-hydroxypropyl)tetramethyl disiloxane (compound of formula (I) in which $R_1$, $R_2$, $R_3$ and $R_4$ are methyl, $R_5$ and $R_6$ are propylene, $R_7$ is O and n is 1).

4. The method according to claim 3, in which the silicon-containing diol of formula (I) is BHTD.

5. The method according to claim 1, in which the diisocyanate is MDI, methylene biscyclohexyl diisocyanate ($H_{12}$MDI), p-phenylene diisocyanate (p-PDI), trans-cyclohexane-1,4-diisocyanate (CHDI), 1,6-diisocyanatohexane (DICH), 1,5-diisocyanatonaphthalene (NDI), para-tetramethylxylenediisocyanate (p-TMXDI), meta-tetramethylxylene diisocyanate (m-TMXDI), 2,4-toluene diisocyanate (2,4-TDI) isomers, isophorone diisocyanate (IPDI), or mixtures thereof.

6. The method according to claim 5, in which the diisocyanate is MDI.

7. The method according to claim 1, in which the $C_{4-12}$alkanediol is BDO, CHDM, 1,6-hexanediol, 1,8-octanediol, 1,9-nonanediol, 1,10-decanediol or 1,13-dodecanediol.

8. The method according to claim 7, in which the $C_{4-12}$alkane diol is BDO.

9. The method according to claim 1, in which weight ratio of siliconcontaining diol: alkanediol is at least about 75:25.

10. The method of claim 1, in which the ratio of prepolymer to alkandiol is in the range of 5:1 to 20:1.

11. The method of claim 1, in which the amount of prepolymer present is 85-92 wt % based on the total weight of the polyurethane.

12. The method according to claim 1, in which the amount of alkanediol is 8-15 wt % based on the total weight of the polyurethane.

13. The method according to claim 1, in which the mixing step (a) is performed by mixing metered amounts of the prepolymer and the diisocyanate in a mixing chamber linked to the vacant cavity.

14. The method according to claim 13, in which the prepolymer has a viscosity in the range of 3,000 to 4,000 centipoise at around 70° C. and is injected into the mixing chamber under a pressure of 10 to 12 bar.

15. The method according to claim 13, in which the alkanediol has a viscosity in the range of 80 to 120 centipoise at room temperature and is injected into the mixing chamber under a pressure of 1 to 3 bar.

16. The method according to claim 13, in which the prepolymer is injected into the mixing chamber at a temperature in the range of 70-90° C.

17. The method according to claim 13, in which the alkanediol is injected into the mixing chamber at a temperature in the range of 25-40° C.

18. The method according to claim 1, in which step (c) allowing the header to cure in the cavity for no more than 20 minutes.

\* \* \* \* \*

UNITED STATES PATENT AND TRADEMARK OFFICE
CERTIFICATE OF CORRECTION

| | |
|---|---|
| PATENT NO. | : 8,801,993 B2 |
| APPLICATION NO. | : 13/504589 |
| DATED | : August 12, 2014 |
| INVENTOR(S) | : Padsalgikar et al. |

It is certified that error appears in the above-identified patent and that said Letters Patent is hereby corrected as shown below:

In the Claims

In column 7, line 62, in Claim 1, delete "1to 3and" and insert --1 to 3 and--, therefor Signed and Sealed this
Twenty-first Day of October, 2014

Michelle K. Lee
*Deputy Director of the United States Patent and Trademark Office*